(12) United States Patent
Green

(10) Patent No.: US 6,555,142 B1
(45) Date of Patent: Apr. 29, 2003

(54) FOOD SUPPLEMENT FORMULATION

(76) Inventor: Lonny S. Green, 10825 Cherry Hill Dr., Glen Allen, VA (US) 23059

( * ) Notice: Subject to any disclaimer, the term of this patent is extended or adjusted under 35 U.S.C. 154(b) by 0 days.

(21) Appl. No.: 10/186,766

(22) Filed: Jul. 1, 2002

(51) Int. Cl.⁷ .................................................. A61K 35/78
(52) U.S. Cl. ........................ 424/725; 424/728; 424/733; 424/641; 424/702; 514/458
(58) Field of Search ................... 424/725, 728, 424/733, 641, 702; 514/458

(56) References Cited

FOREIGN PATENT DOCUMENTS

JP             07053394 A    *   2/1995

OTHER PUBLICATIONS

Jiezhong (Journal of Chinese Medicine (1997), No. 53).*
www.herbalists.on.ca/resources/freeman/ALPINA.html; 2001.*

* cited by examiner

*Primary Examiner*—Francisco Prats
*Assistant Examiner*—Susan D. Coe
(74) *Attorney, Agent, or Firm*—Donald R. Fraser

(57) ABSTRACT

A food supplement formulation comprises yi zhi ren, shan zhu yu, wu wei zi, ginseng, valerian root, passiflora incarnate, L-methionine, L-arginine, and a gender-specific complex selected from the group consisting of a mixture comprising beta-sitosteroi, saw palmetto, pollen extract, selenium, zinc, vitamin E, and lycopene, and a mixture comprising black cohosh, genistein, vitamin E, and cramp bark.

60 Claims, No Drawings

FOOD SUPPLEMENT FORMULATION

FIELD OF THE INVENTION

The present invention relates generally to a food supplement formulation. More particularly, the invention is directed to a food supplement formulation which may additionally aid bladder control.

BACKGROUND OF THE INVENTION

Herbal and mineral formulations have been used as dietary supplements and natural medicaments for many years. In addition to providing compounds necessary to the human body for good nutrition, such formulations additionally may aid the body in dealing with a number of urinary tract maladies.

In addition to desiring a supplement to the daily diet, many persons suffer from a condition known as "overactive bladder," wherein the patient has difficulty controlling urinary flow.

It would be desirable to prepare an herbal and mineral formulation that would act as a food supplement and might also simultaneously relieve the symptoms and manifestations of overactive bladder.

SUMMARY OF THE INVENTION

Accordant with the present invention, a beneficial herbal and mineral food supplement formulation has surprisingly been discovered. It comprises: yi zhi ren, shan zhu yu, wu wei zi, ginseng, valerian root, passiflora incarnata, L-methionine, L-arginine, and a gender-specific complex selected from the group consisting of a mixture comprising beta-sitosterol, saw palmetto, pollen extract, selenium, zinc, vitamin E, and lycopene, and a mixture comprising black cohosh, genistein, vitamin E, and cramp bark.

The food supplement formulation according to the present invention is useful to supplement the daily human diet, and additionally may be particularly useful as a bladder control agent.

DETAILED DESCRIPTION OF THE PREFERRED EMBODIMENT

The present invention is directed to a food supplement formulation comprising yi zhi ren; shan zhu yu; wu wei zi; ginseng; valerian root; passiflora incarnata; L-methionine; L-arginine; and a gender-specific complex selected from the group consisting of a mixture comprising beta-sitosterol, saw palmetto, pollen extract, selenium, zinc, vitamin E, and lycopene, and a mixture comprising black cohosh, genistein, vitamin E, and cramp bark.

Yi zhi ren is a well-known herb useful as an agent to ease abdominal pain and control urinary incontinence and loose bowels. Yi zhi ren may be present in the inventive formulation at a concentration ranging from about 7 to about 22 weight percent. Preferably, the concentration of yi zhi ren ranges between about 14.1 and about 16.6 weight percent.

Shan zhu yu is a well-known herb which acts to reduce bodily secretion such as, for example, to relieve excessive sweating and urinary flow. Shan zhu yu may be present in the inventive formulation at a concentration ranging from about 7 to about 22 weight percent. Preferably, the concentration of shan zhu yu ranges between about 14.1 and about 16.6 weight percent.

Wu wei zi is a well-known herb useful to control profuse sweating and chronic thirst. Wu wei zi may be present in the inventive formulation at a concentration ranging from about 5 to about 15 weight percent. Preferably, the concentration of wu wei zi ranges between about 10.7 and about 12.7 weight percent.

Ginseng is a well-known herb which acts to relieve dyspepsia, vomiting, and nervous disorders. Ginseng may be present in the inventive formulation at a concentration ranging from about 3 to about 12 weight percent. Preferably, the concentration of ginseng ranges between about 7.3 and about 8.6 weight percent.

Valerian root is a well-known herb useful to treat sleeplessness, muscle cramps, pain, and spasms. Valerian root may be present in the inventive formulation at a concentration ranging from about 2 to about 7 weight percent. Preferably, the concentration of valerian root ranges between about 3.6 and about 4.2 weight percent.

Passiflora incarnata is a well-known herb which acts as a sedative and aid in the treatment of spasms and nervousness. Passiflora incarnata may be present in the inventive formulation at a concentration ranging from about 7 to about 22 weight percent. Preferably, the concentration of passiflora incarnata ranges between about 14.1 and about 16.6 weight percent.

L-methionine is a well-known amino acid useful to assist detoxification of the human body. L-methionine may be present in the inventive formulation at a concentration ranging from about 0.1 to about 1.5 weight percent. Preferably, the concentration of L-methionine ranges between about 0.6 and about 0.8 weight percent.

L-arginine is a well-known amino acid which acts to aid the body's immune system and as a precursor to the production of nitric oxide which assists bladder control. L-arginine may be present in the inventive formulation at a concentration ranging from about 1 to about 10 weight percent. Preferably, the concentration of L-arginine ranges between about 4.3 and about 5.1 weight percent.

Beta-sitosterol is a well-known herb useful to reduce levels of cholesterol in the human bloodstream and to block the absorption of cholesterol. Beta-sitosterol may optionally be present in the inventive formulation at a concentration ranging from about 2 to about 7 weight percent. Preferably, the concentration of beta-sitosterol if present is about 4.3 weight percent.

Saw palmetto is a well-known herb which acts to improve the functioning of the prostate and urinary tract in men. Saw palmetto may optionally be present in the inventive formulation at a concentration ranging from about 4 to about 10 weight percent. Preferably, the concentration of saw palmetto if present is about 6.9 weight percent.

Pollen extract is a well-known herbal product useful as an antioxidant. Pollen extract may optionally be present in the inventive formulation at a concentration ranging from about 3 to about 8 weigh percent. Preferably, the concentration of pollen extract if present is about 5.4 weight percent.

Selenium is a well-known mineral which acts as an antioxidant and to enhance the body's immunity. Selenium may optionally be present in the inventive formulation at a concentration ranging from about 2 to about 7 weight percent. Preferably, the concentration of selenium if present is about 4.3 weight percent.

Zinc is a well-known mineral useful as an anti-inflammation agent. Zinc may optionally be present in the inventive formulation at a concentration ranging from about 0.3 to about 3 weight percent. Preferably, the concentration of zinc if present is about 1.1 weight percent.

Vitamin E is a well-known natural compound which acts as an antioxidant and to boost the human immune system. Vitamin E may be present in the inventive formulation at a concentration ranging from about 4 to about 15 weight percent. Preferably, the concentration of vitamin E ranges between about 8.6 and about 10.2 weight percent.

Lycopene is a well-known compound useful as an antioxidant. Lycopene may optionally be present in the inventive formulation at a concentration ranging from about 0.2 to about 2 weight percent. Preferably, the concentration of lycopene if present is about 0.6 weight percent.

Black cohosh is a well-known herb which acts to control diarrhea and alleviate general weakness. Black cohosh may optionally be present in the inventive formulation at a concentration ranging from about 1.2 to about 4 weight percent. Preferably, the concentration of black cohosh if present is about 2 weight percent.

Genistein is a well-known compound useful to inhibit the growth of blood vessels in the human body. Genistein may optionally be present in the inventive formulation at a concentration ranging from about 2 to about 8 weight percent. Preferably, the concentration of genistein if present is about 5.1 weight percent.

Cramp bark is a well-known herb which acts as an antispasmodic and astringent. Cramp bark may optionally be present in the inventive formulation at a concentration ranging from about 0.5 to about 3 weight percent. Preferably, the concentration of cramp bark if present is about 1.5 weight percent.

The aforementioned ingredients may be ground and mixed together by conventional mixing techniques. Thereafter, the powdered mixture may be pressed into tablets or placed in gelatin capsules for oral administration. The inventive food supplement formulation may additionally contain conventional fillers and extenders such as, for example, rice flower. Conveniently, the inventive food supplement formulation may be taken orally at a dosage rate ranging from about 500 to about 4,000 milligrams per day. Preferably, the dosage rate effective as a food supplement and possibly a bladder control agent ranges from about 1,800 to about 2,500 milligrams per day.

The inventive food supplement formulation is customized depending upon whether it might provide the additional benefit of bladder control for a man or a woman. Thus, the food supplement formulation is gender-specific.

EXAMPLE

The ingredients recited above are ground and mixed together in the quantities set forth in the following Table.

TABLE

Food Supplement Formulation

| Ingredient | Male-Specific Wt. % | Female-Specific Wt. % |
| --- | --- | --- |
| yi zhi ren | 14.1 | 16.6 |
| shan zhi yu | 14.1 | 16.6 |
| wu wei zi | 10.7 | 12.7 |
| ginseng | 7.3 | 8.6 |
| valerian root | 3.6 | 4.2 |
| passiflora incarnata | 14.1 | 16.6 |
| L-methionine | 0.6 | 0.8 |
| L-arginine | 4.3 | 5.1 |
| beta-sitosterol | 4.3 | |
| saw palmetto | 6.9 | |
| pollen extract | 5.4 | |
| selenium | 4.3 | |
| zinc | 1.1 | |
| vitamin E | 8.6 | 10.2 |
| lycopene | 0.6 | |
| black cohosh | | 2.0 |
| genistein | | 5.1 |
| cramp bark | | 1.5 |
| Total | 100.0 | 100.0 |

The invention is more easily comprehended by reference to the specific embodiments recited hereinabove which are representative of the invention. It must be understood, however, that the specific embodiments are provided only for the purpose of illustration, and that the invention may be practiced otherwise than as specifically illustrated without departing from its spirit and scope.

What is claimed is:

1. A food supplement formulation, comprising:
   yi zhi ren;
   shan zhu yu;
   wu wei zi;
   ginseng;
   valerian root;
   passiflora incarnata;
   L-methionine;
   L-arginine; and
   a gender-specific complex selected from the group consisting of a mixture comprising beta-sitosterol, saw palmetto, pollen extract, selenium, zinc, vitamin E, and lycopene, and a mixture comprising black cohosh, genistein, vitamin E, and cramp bark.

2. The food supplement formulation according to claim 1, wherein the concentration of yi zhi ren ranges from about 7 to about 22 weight percent.

3. The food supplement formulation according to claim 2, wherein the concentration of yi zhi ren ranges from about 14.1 to about 16.6 weight percent.

4. The food supplement formulation according to claim 1, wherein the concentration of shan zhu yu ranges from about 7 to about 22 weight percent.

5. The food supplement formulation according to claim 4, wherein the concentration of shan zhu yu ranges from about 14.1 to about 16.6 weight percent.

6. The food supplement formulation according to claim 1, wherein the concentration of wu wei zi ranges from about 5 to about 15 weight percent.

7. The food supplement formulation according to claim 6, wherein the concentration of wu wei zi ranges from about 10.7 to about 12.7 weight percent.

8. The food supplement formulation according to claim 1, wherein the concentration of ginseng ranges from about 3 to about 12 weight percent.

9. The food supplement formulation according to claim 8, wherein the concentration of ginseng ranges from about 7.3 to about 8.6 weight percent.

10. The food supplement formulation according to claim 1, wherein the concentration of valerian root ranges from about 2 to about 7 weight percent.

11. The food supplement formulation according to claim 10, wherein the concentration of valerian root ranges from about 3.6 to about 4.2 weight percent.

12. The food supplement formulation according to claim 1, wherein the concentration of passiflora incarnata ranges from about 7 to about 22 weight percent.

13. The food supplement formulation according to claim 12, wherein the concentration of passiflora incarnata ranges from about 14.1 to about 16.6 weight percent.

14. The food supplement formulation according to claim 1, wherein the concentration of L-methionine ranges from about 0.1 to about 1.5 weight percent.

15. The food supplement formulation according to claim 14, wherein the concentration of L-methionine ranges from about 0.6 to about 0.8 weight percent.

16. The food supplement formulation according to claim 1, wherein the concentration of L-arginine ranges from about 1 to about 10 weight percent.

17. The food supplement formulation according to claim 16, wherein the concentration of L-arginine ranges from about 4.3 to about 5.1 weight percent.

18. The food supplement formulation according to claim 1, wherein the concentration of beta-sitosterol ranges from about 2 to about 7 weight percent.

19. The food supplement formulation according to claim 18, wherein the concentration of beta-sitosterol is about 4.3 weight percent.

20. The food supplement formulation according to claim 1, wherein the concentration of saw palmetto ranges from about 4 to about 10 weight percent.

21. The food supplement formulation according to claim 20, wherein the concentration of saw palmetto is about 6.9 weight percent.

22. The food supplement formulation according to claim 1, wherein the concentration of pollen extract ranges from about 3 to about 8 weight percent.

23. The food supplement formulation according to claim 22, wherein the concentration of pollen extract is about 5.4 weight percent.

24. The food supplement formulation according to claim 1, wherein the concentration of selenium ranges from about 2 to about 7 weight percent.

25. The food supplement formulation according to claim 24, wherein the concentration of selenium is about 4.3 weight percent.

26. The food supplement formulation according to claim 1, wherein the concentration of zinc ranges from about 0.3 to about 3 weight percent.

27. The food supplement formulation according to claim 26, wherein the concentration of zinc is about 1.1 weight percent.

28. The food supplement formulation according to claim 1, wherein the concentration of vitamin E ranges from about 4 to about 15 weight percent.

29. The food supplement formulation according to claim 28, wherein the concentration of vitamin E ranges from about 8.6 to about 10.2 weight percent.

30. The food supplement formulation according to claim 1, wherein the concentration of lycopene ranges from about 0.2 to about 2 weight percent.

31. The food supplement formulation according to claim 30, wherein the concentration of lycopene is about 0.6 weight percent.

32. The food supplement formulation according to claim 1, wherein the concentration of black cohosh ranges from about 1.2 to about 4 weight percent.

33. The food supplement formulation according to claim 32, wherein the concentration of black cohosh is about 2 weight percent.

34. The food supplement formulation according to claim 1, wherein the concentration of genistein ranges from about 2 to about 8 weight percent.

35. The food supplement formulation according to claim 34, wherein the concentration of genistein is about 5.1 weight percent.

36. The food supplement formulation according to claim 1, wherein the concentration of cramp bark ranges from about 0.5 to about 3 weight percent.

37. The food supplement formulation according to claim 36, wherein the concentration of cramp bark is about 1.5 weight percent.

38. The food supplement formulation according to claim 1, wherein the gender-specific complex is a mixture comprising beta-sitosterol, saw palmetto, pollen extract, selenium, zinc, vitamin E, and lycopene.

39. The food supplement formulation according to claim 1, wherein the gender-specific complex is a mixture comprising black cohosh, genistein, vitamin E, and cramp bark.

40. A food supplement formulation comprising
 about 7 to about 22 weight percent yi zhi ren;
 about 7 to about 22 weight percent shan zhu yu;
 about 5 to about 16 weight percent wu wei zi;
 about 3 to about 12 weight percent ginseng;
 about 2 to about 7 weight percent valerian root;
 about 7 to about 22 weight percent passiflora incarnata;
 about 0.1 to about 1.5 weight percent L-methionine;
 about 1 to about 10 weight percent L-arginine; and
 a gender-specific complex selected from the group consisting of a mixture comprising about 2 to about 7 weight percent beta-sitosterol, about 4 to about 10 weight percent saw palmetto, about 3 to about 8 weight percent pollen extract, about 2 to about 7 weight percent selenium, about 0.3 to about 3 weight percent zinc, about 4 to about 12 weight percent vitamin E, and about 0.2 to about 2 weight percent lycopene, and a mixture comprising about 1.2 to about 4 weight percent black cohosh, about 2 to about 8 weight percent genistein, about 5 to about 15 weight percent vitamin E, and about 0.5 to about 3 weight percent cramp bark.

41. The food supplement formulation according to claim 40, wherein the concentration of yi zhi ren ranges from about 14.1 to about 16.6 weight percent.

42. The food supplement formulation according to claim 40, wherein the concentration of shan zhu yu ranges from about 14.1 to about 16.6 weight percent.

43. The food supplement formulation according to claim 40, wherein the concentration of wu wei zi ranges from about 10.7 to about 12.7 weight percent.

44. The food supplement formulation according to claim 40, wherein the concentration of ginseng ranges from about 7.3 to about 8.6 weight percent.

45. The food supplement formulation according to claim 40, wherein the concentration of valerian root ranges from about 3.6 to about 4.2 weight percent.

46. The food supplement formulation according to claim 40, wherein the concentration of passiflora incarnata ranges from about 14.1 to about 16.6 weight percent.

47. The food supplement formulation according to claim 40, wherein the concentration of L-methionine ranges from about 0.6 to about 0.8 weight percent.

48. The food supplement formulation according to claim 40, wherein the concentration of L-arginine ranges from about 4.3 to about 5.1 weight percent.

49. The food supplement formulation according to claim 40, wherein the concentration of beta-sitosterol is about 4.3 weight percent.

50. The food supplement formulation according to claim 40, wherein the concentration of saw palmetto is about 6.9 weight percent.

51. The food supplement formulation according to claim 40, wherein the concentration of pollen extract is about 5.4 weight percent.

52. The food supplement formulation according to claim 40, wherein the concentration of selenium is about 4.3 weight percent.

53. The food supplement formulation according to claim 40, wherein the concentration of zinc is about 1.1 weight percent.

54. The food supplement formulation according to claim 40, wherein the concentration of vitamin E ranges from about 8.6 to about 10.2 weight percent.

55. The food supplement formulation according to claim 40, wherein the concentration of lycopene is about 0.6 weight percent.

56. The food supplement formulation according to claim 40, wherein the concentration of black cohosh is about 2 weight percent.

57. The food supplement formulation according to claim 40, wherein the concentration of genistein is about 5.1 weight percent.

58. The food supplement formulation according to claim 40, wherein the concentration of cramp bark is about 1.5 weight percent.

59. The food supplement formulation according to claim 40, wherein the gender-specific complex is a mixture comprising beta-sitosterol, saw palmetto, pollen extract, selenium, zinc, vitamin E, and lycopene.

60. The food supplement formulation according to claim 40, wherein the gender-specific complex is a mixture comprising black cohosh, genistein, vitamin E, and cramp bark.

* * * * *

UNITED STATES PATENT AND TRADEMARK OFFICE
CERTIFICATE OF CORRECTION

PATENT NO.   : 6,555,142 B1
DATED        : April 29, 2003
INVENTOR(S)  : Lonny S. Green It is certified that error appears in the above-identified patent and that said Letters Patent is hereby corrected as shown below:

<u>Title page,</u>
Item [57], ABSTRACT,
Line 3, replace word "incarnate" with -- incarnata -- and
Line 5, replace word "beta-sitosteroi" with -- beta-sitosterol --

Signed and Sealed this

Second Day of September, 2003

JAMES E. ROGAN
*Director of the United States Patent and Trademark Office*